United States Patent [19]

Lombardo

[11] Patent Number: 5,280,378
[45] Date of Patent: Jan. 18, 1994

[54] CYCLICALLY SCANNED MEDICAL LASER
[75] Inventor: Igino Lombardo, Sharon, Mass.
[73] Assignee: I.L. Med, Inc., Walpole, Mass.
[21] Appl. No.: 600,489
[22] Filed: Oct. 19, 1990
[51] Int. Cl.$^5$ .......................................... G02B 26/08
[52] U.S. Cl. .................... 359/199; 359/200; 359/209; 359/214
[58] Field of Search ......... 359/196–200, 212–214, 223, 225, 226; 310/36, 40R, 40mm, 46, 66, 75R, 91, 179, 208

[56] References Cited

U.S. PATENT DOCUMENTS

| | | | |
|---|---|---|---|
| 4,069,823 | 1/1978 | Isakov et al. | 128/303.1 |
| 4,122,853 | 10/1978 | Smith | 128/303.1 |
| 4,215,694 | 8/1980 | Isakov et al. | 128/303.1 |
| 4,364,000 | 12/1982 | Burke | 359/212 |
| 4,566,453 | 1/1986 | Kumano et al. | 128/303.1 |
| 4,627,685 | 12/1986 | Sakuma | 359/212 |
| 4,638,800 | 1/1987 | Michel | 128/303.1 |
| 4,658,817 | 4/1987 | Hardy | 128/303.1 |
| 4,871,904 | 10/1989 | Metlitsky et al. | 359/212 |
| 4,902,083 | 2/1990 | Wells | 359/223 |
| 4,930,848 | 6/1990 | Knowles | 359/214 |
| 4,990,808 | 2/1991 | Paulsen | 359/214 |

Primary Examiner—Bruce Y. Arnold
Assistant Examiner—James Phan
Attorney, Agent, or Firm—Weingarten, Schurgin, Gagnebin & Hayes

[57] ABSTRACT

A medical laser system for scanning a beam of laser light including an oscillating mirror that repeatedly scans a laser beam in a cyclical pattern, such as a circle or an ellipse, or in a zig-zag pattern within a defined boundary. The oscillating mirror can be included in a myringotomy instrument. Also, the oscillating mirror can be included in a joystick-controlled medical laser system, or in any other system where a cyclically scanned laser beam is useful.

8 Claims, 5 Drawing Sheets

CYCLICALLY SCANNED MEDICAL LASER

FIELD OF THE INVENTION

This invention relates to medical laser systems, and more particularly to laser systems providing a scanned laser beam.

BACKGROUND OF THE INVENTION

There are surgical procedures that employ a laser to vaporize a portion of tissue. For example, a Carbon Dioxide ($CO_2$) or Argon Ion laser is used to perform a myringotomy, wherein a 1 mm diameter hole is made in an ear drum. To accomplish this, a surgeon focuses the laser optics to provide a 1 mm spot size. The laser is then energized for a period of 50 to 100 msec, emitting a pulse of laser light that vaporizes the ear drum tissue upon contact, leaving a 1 mm hole. The vaporization of the tissue is believed to cause an acoustic shock wave in the ear drum that is perceived by the patient as an abrupt, loud noise, described as a "pop" sound. Children most likely perceive the noise as painful and disturbing, and are often reluctant to submit to the procedure again. Furthermore, since the intensity of the laser spot is typically described by a Gaussian distribution, only the central portion of the spot has an intensity sufficient to vaporize tissue. The outer skirt of the spot induces tissue charring and coagulation, which can be undesirable side-effects of current techniques.

The stapes is the smallest of three small bones that together transmit sound from the ear drum and ultimately to the auditory nerve. Normally, the stapes presses against the vestibular window. If the stapes should become fixed to the vestibular window such that sound cannot be effectively transmitted, then impaired hearing results. To remedy this, a small hole is made in the stapes. A prosthetic device is inserted in the hole such that the prosthetic device extends toward and contacts the vestibular window. Thus, sound can again be effectively transmitted. One current technique for making the small hole is to form a circular array of closely spaced, yet smaller holes, and then remove the circular region surrounded by the smaller holes. The prosthetic device is then inserted in the now-vacant region. However, it is difficult and time-consuming for a surgeon to precisely position the laser beam and fire the laser to produce the circular array of smaller holes. Due to lack of precision, the shape of the circular region may not closely conform to the shape of the prosthesis, resulting in poor contact of the prosthetic device with the vestibular window, thereby creating a possibility of perilymph leakage and dislodging of the prosthetic device, resulting in renewed hearing impairment.

SUMMARY OF THE INVENTION

The medical laser system of the invention provides an apparatus for cyclically scanning a beam of laser light. The apparatus includes a mirror that is driven into oscillation so as to repeatedly scan a laser beam in a cyclical pattern, such as a circle, an ellipse, or a zig-zag within a rectangular or other defined boundary. The laser beam is scanned in one embodiment by a rotating mirror that is fixed such that the plane of the mirror is not perpendicular to its axis of rotation. Alternatively, the beam can be scanned by a resiliently supported mirror and driven into oscillation by a pair of solenoids that are energized by a pair of controllably-phased periodic energizing sources. The mirror can be included in a myringotomy instrument. Also, the mirror can be included in a joystick-controlled medical laser system, or in any other medical or other system where a cyclically scanned laser beam is useful.

When included in an otoscope to perform a myringotomy, the mirror is preferably scanned in a circular or elliptical pattern to cause the beam of laser light to cut around a region of tissue to be removed, without vaporizing the entire region, thereby providing a hole in the ear drum. Since only a small region of tissue is vaporized at any given time, the associated shock wave is substantially less than that produced if the hole in the ear drum were to be vaporized by a single stationary laser pulse. Thus, the invention practically eliminates the loud noise typically experienced during a myringotomy. Furthermore, tissue charring is greatly reduced, thereby improving healing. Also, when included in a joystick-controlled medical laser system, less surgical time and skill are required to perform a myringotomy or to produce a hole in the stapes for inserting a prosthetic device, and the hole so-produced has a more uniform and repeatable shape. Laser light of a wide variety of wavelengths can be employed, and for certain wavelengths, a dye or a chromophore can be applied to the tissue to enhance absorption of laser light, thereby enhancing its cutting action.

The medical laser system for scanning a beam of laser light can also include a beam-guiding optical fiber with a transmissive tip, the fiber being cooperative with means for cyclically oscillating the transmissive tip to cause a laser beam to be scanned in a cyclical or zig-zag pattern.

DESCRIPTION OF THE DRAWING

The invention will be more fully understood from the following detailed description, in conjunction with the accompanying figures, in which.

DETAILED DESCRIPTION OF THE INVENTION

Figure 1:
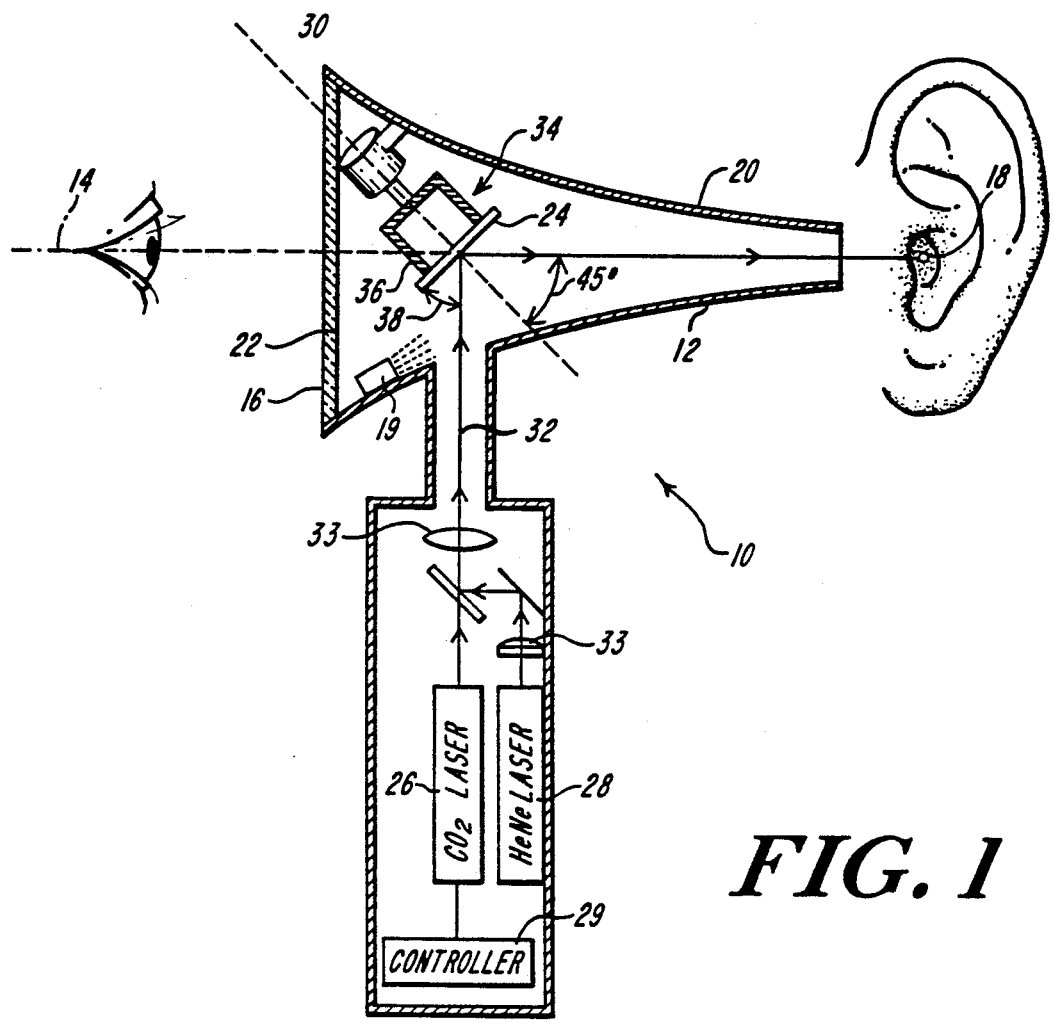
FIG. 1 is side view of an embodiment of a scanned laser that includes a rotating mirror.

With reference to FIG. 1, a myringotomy instrument generally designated by the reference numeral 10 includes a hollow viewing piece 12 with a central longitudinal axis 14. The viewing piece 12 has a viewing end 16 for viewing a target tympanic membrane (ear drum) 18. An auricular insertion end 20 is inserted into a patient's ear so that the ear drum 18 comes into view. Viewing optics 22 disposed at the viewing end provides magnification of a target site on the ear drum 18. An illumination source 19, disposed within the viewing piece 1 and between the viewing end 16 and the insertion end 20, illuminates the target site. The source 19 can be a fiber optic cable coupled to a light source, or can be any other source of light disposed to illuminate the ear drum.

A rotating mirror 24 includes a surface of a substrate that is adapted to reflect heating laser light, such as produced by a $CO_2$ (carbon dioxide) heating laser 26 and visible light, such as produced by a HeNe (helium-neon) targeting laser 28 (or a solid state laser or a semiconductor laser), while retaining the capacity to transmit visible light reflected by the ear drum 18. The heating laser 26 typically has a power of 1-4 watts. The surface can be substantially planar, or it can be substantially spherical to provide beam focusing. The rotating mirror 24 is disposed between the viewing end 16 and the insertion end 20 of the viewing piece 12. In a preferred embodiment, the mirror 24 is oriented such that its center is substantially coincident with the central axis 14, while the axis of rotation 30 of the mirror 24 is inclined at an angle of 45° with respect to the central axis 14. The mirror 24 may also be disposed in an off-axis position, thereby permitting the use of substrate and mirror materials that are not transparent to visible light.

In a first embodiment, the mirror 24 is rigidly mounted on a forked structure 34, including plural legs 36, such that the plane of mirror 24 is not orthogonal to the axis of rotation 30, while the center of the mirror 24 is substantially coincident with a point on the axis 30. Rotation of the mirror 24 provides periodic changes in orientation of its reflecting surface with respect to the central axis 14, a composite laser beam 32 and the surface of the ear drum 18, thereby providing a cyclical laser scan pattern on the ear drum.

Figure 2:
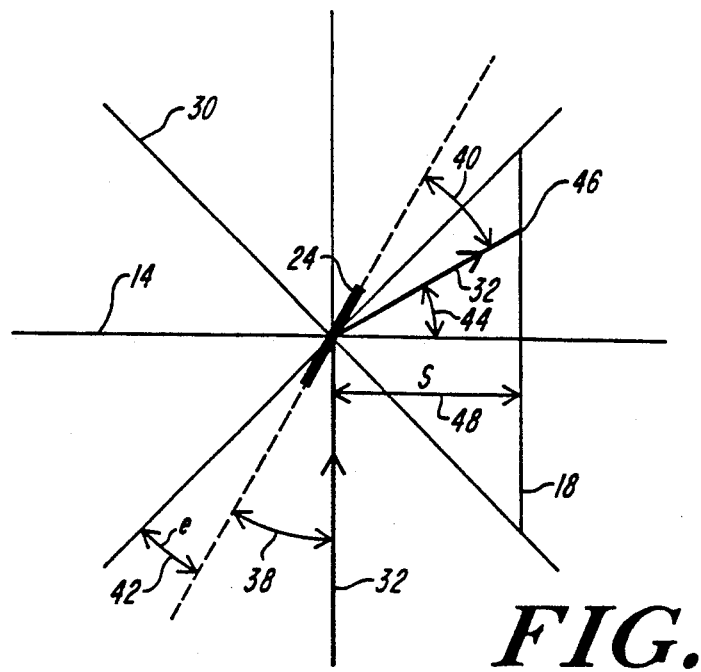
FIG. 2 is a ray tracing of a laser beam reflected by an orientable mirror.

With reference to FIG. 2, the laser beam 32 is directed towards the center of the mirror 24. The beam 32 includes the superposition of the beams emitted by the heating $CO_2$ laser 26 and the targeting HeNe laser 28, respectively. The beam 32 passes through beam shaping optics 33 as shown in FIG. 1 to focus the laser beam on the ear drum 18 in a manner known to those skilled in the art. The beams from both lasers 26 and 28 are reflected at the surface of the mirror 24 for all angular orientations of the mirror 24, and strike the ear drum 18 at a point 46, which is disposed at different locations on the ear drum throughout a complete revolution of the mirror 24 about the axis 30, thereby describing an ellipse. The angle of reflection 40 of the beam 32 is substantially equal to the angle of incidence 38 of the beam 32. A tilt 'e' 42 of the mirror 24 is the difference between 45° and the angle of incidence 38, and therefore the tilt 42 determines the angle of incidence 38, and therefore the angle of reflection 40. The tilt 42 of the mirror 24 determines the angle of attack 44. For each value of the tilt 42, the size of the elliptical hole produced by a full scan of the laser beam 32 is determined by the distance 'S' 48 of the mirror 24 from the ear drum 18.

Figure 3A:
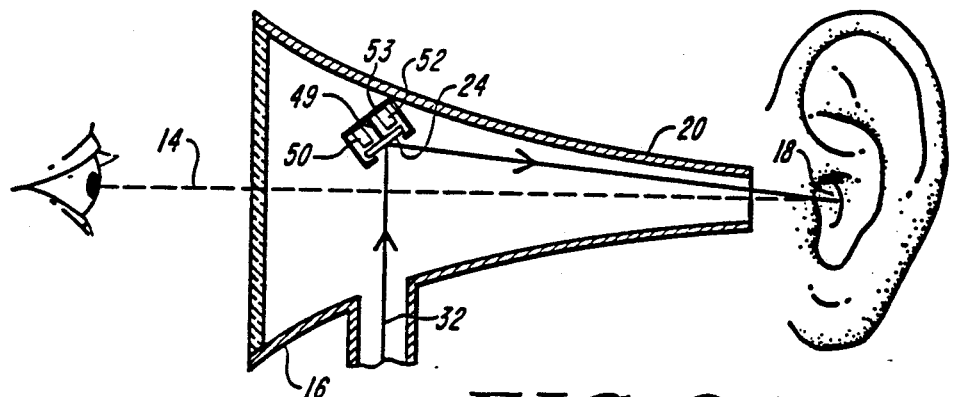
FIG. 3A is a side view of an embodiment that includes a pair of solenoids for driving a resiliently supported mirror.
Figure 3B:
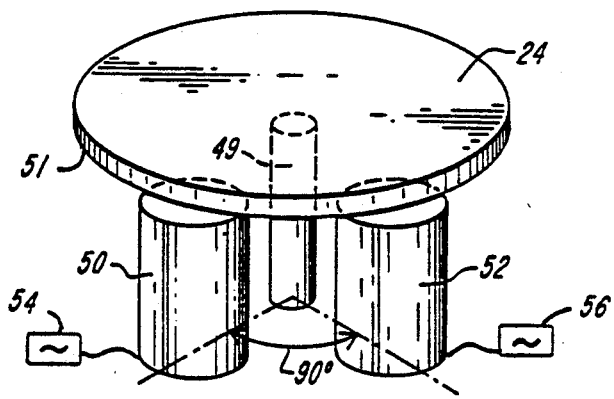
FIG. 3B is a side view of the solenoids and mirror of FIG. 3A.

In a second embodiment, shown in FIG. 3A, the mirror 24 is disposed in a position off the central axis 14 so that the user has an unobstructed view of the ear drum 18. With reference to FIG. 3B, the mirror 24 is supported by a resilient filament 49. One end of the filament 49 is bonded to the center of the backside 51 of the mirror, and the other end is bonded to a casing 53. The mirror's substrate is coated on its backside 51 with, or otherwise fixed to, a magnetic material adapted to interact with a magnetic field originating from a pair of solenoids 50 and 52 disposed in proximity to the mirror 24, and separated by 90° from each other with respect to the filament 49.

The solenoids 50 and 52 can be driven by power sources 54 and 56 to produce a periodically changing magnetic field in the vicinity of the substrate. Power sources 54 and 56 are connected to respective solenoids 50 and 52. By varying the phase relationship between the power sources, the shape of a scan pattern upon the ear drum 18 can be changed.

Figure 4A:
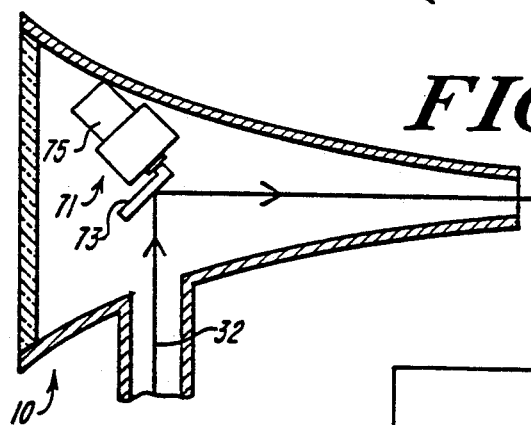
FIG. 4A is a side view of an embodiment of a scanned laser that includes a motorized gimbal mirror mount.
Figure 4B:
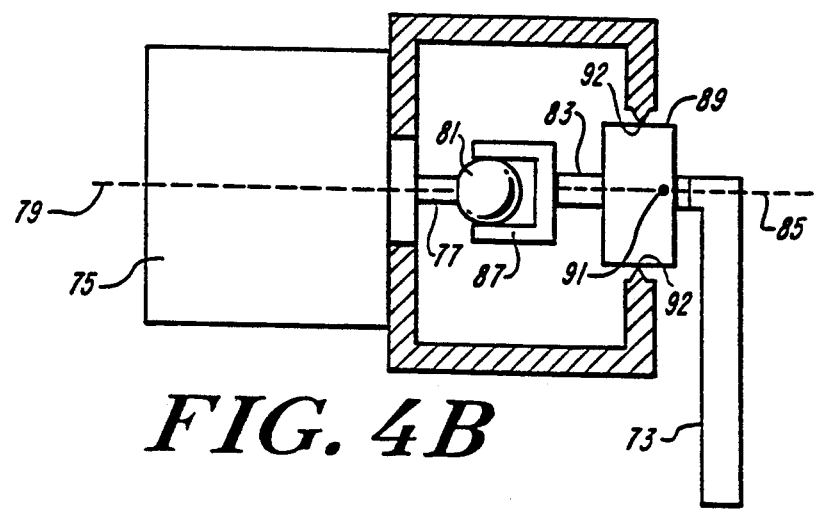
FIG. 4B is a side view of the motorized gimbal mirror mount of FIG. 4A.

In a third embodiment, shown in FIGS. 4A and 4B, cyclical scanning of the targeted laser beam 32 is performed by the assembly generally designated by reference numeral 71. The assembly 71 is incorporated within a myringotomy instrument 10. Furthermore, the assembly 71 is disposed such that its mirror assembly 73 is disposed in the path of the laser beam 32.

A motor assembly 75 is operative to rotate a shaft 77 about an axis 79. The shaft 77 is fixed to a ball 81 that is mounted eccentrically such that a shaft 83 with a central axis 85 is effectively non-concentric with respect to the shaft 77. Thus, when the shaft 77 rotates, the shaft 83 will describe a circular path centered on the axis 79. The ball 81 rides within a hollow sleeve 87. The sleeve 87 is fixed to the shaft 83 that is fixed to a gimbal 89 that enables the shaft 83 to pivot with two degrees of freedom about points 91 and 92. Rotation of the shaft 77 will result in a cyclical pivoting motion of the shaft 83 through two degrees of freedom. Pivot points 91 and 92 are separated so as to create a predetermined ratio in the movement of the mirror surface 73 when pivoting around points 91 and 92, respectively, thereby converting an otherwise resulting elliptical pattern into a circular pattern.

Figure 5:
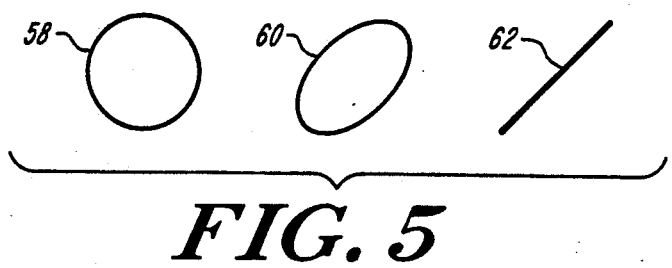
FIG. 5 is a collection of cyclic scan patterns.

To perform a myringotomy with the instrument of the invention, the physician inserts the insertion end 20 into the patient's ear, bringing the ear drum 18 into view. The HeNe laser 28 is turned on first to provide a visible, non-destructive indication of the size, shape, and position of the circularly scanned laser beam. The size and shape of the scan of the embodiment of FIG. 3A can be changed by varying the amplitude and phase relationship between the power sources 54 and 56. Referring to FIG. 5, if the power sources are in quadrature, a circular 58 or elliptical 60 scan pattern is traced, depending on the amplitude applied by the power sources. If the respective phases of the power sources 54 and 56 differ by 45°, an elliptical pattern 60 is formed. If there is no phase difference, a straight line 62 is traced. The position of the scanned beam is controlled by manually changing the orientation of the entire instrument 10.

In addition to properly sizing and targeting the scanned beam 32, the physician must choose the number of scan cycles for which the heating laser 26 will impinge upon the tissue. A simple controller 29, which can be internal to or externally connected to the instrument 10 via a suitable umbilical cord, determines how long the heating laser 26 must be energized to provide the desired number of scan cycles, given the rate of change of angular orientation of the mirror 24. In this embodiment, the typical period of a scan is 50 msec. Once all the above mentioned parameters are set, the controller 29 is activated, the heating laser 26 is energized, and the beam 32 is scanned for a desired number of cycles. The controller 29 can additionally provide the necessary power to drive the lasers 26 and 28.

Figure 6A:
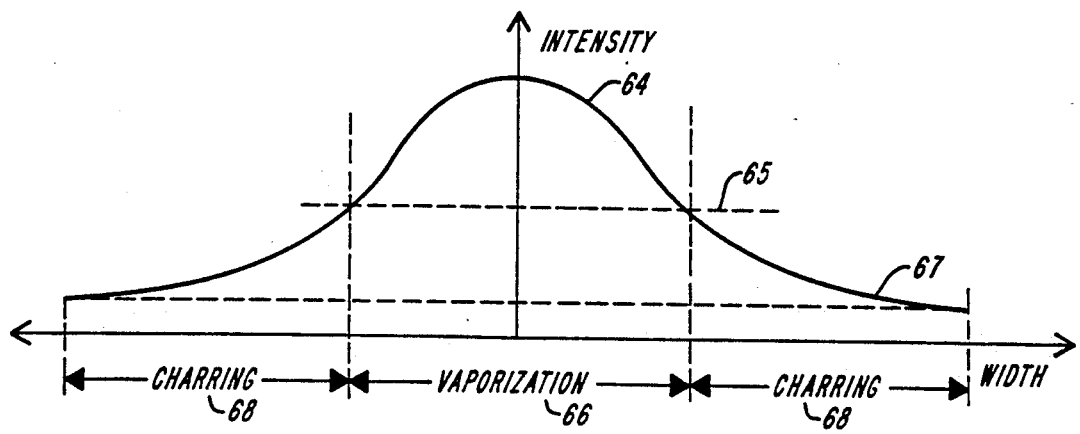
FIG. 6A is a graph of laser intensity plotted against distance from the center of a prior art laser beam.

The beam 32 of the invention is substantially narrower than the beam that is typically employed to create a hole in a tympanic membrane. With reference to FIG. 6A, a typical common beam profile 64 is shown for purposes of comparison, where beam intensity is plotted as a function of position within the beam, describing a Gaussian function along an arbitrary direction perpendicular to the beam. Commonly, a zone of vaporization 66 of the profile 64, where the beam intensity exceeds a vaporization threshold 65, corresponds to the hole produced by the beam. The hole is skirted by a ring of charred tissue 68, bound by a charring threshold 67. Charring of tissue is undesirable.

Figure 6B:
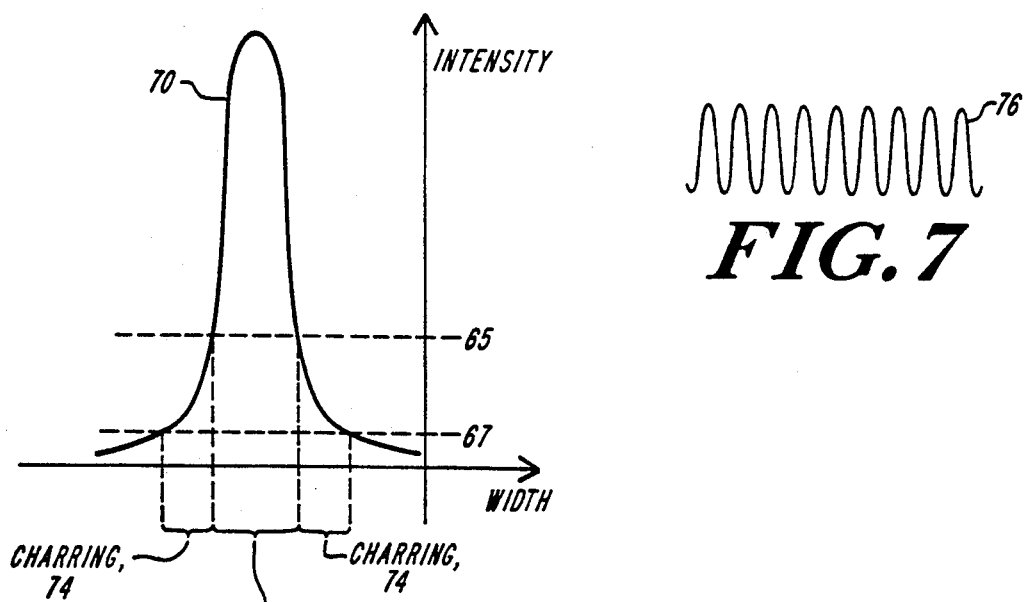
FIG. 6B is a graph of laser intensity plotted against distance from the center of a relatively narrow beam of the invention.

Referring to FIG. 6B, the invention provides a relatively narrow beam profile 70, also a Gaussian profile, but with a smaller vaporization zone 72 and charring ring 74. Thus, the hole produced by this beam is smaller and is surrounded by a narrower ring of charred tissue than the beam shown in FIG. 6A.

To create a hole of the size produced by the beam in FIG. 6A, the beam of FIG. 6B is scanned in a pattern that encloses an area the size of the hole. The portion of the tympanic membrane that lies within the circular scan pattern is then easily removed, or falls away. The resulting hole is clean and relatively free of charred tissue. Furthermore, the narrower beam of FIG. 6B produces less noise as perceived by the patient because the vaporization region is much smaller than the vaporization region of FIG. 6A.

Figure 7:
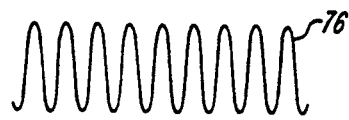
FIG. 7 is a depiction of a cyclical linearly scanned beam translated in a direction perpendicular to the direction of linear scanning.

To create a rectangular hole, the phase between the two power sources is set to zero to produce a straight line scan pattern, and the instrument itself is scanned in a direction perpendicular to the scan of the mirror 24 for a duration of many cycles, to produce a pattern 76, as shown in FIG. 7. Alternatively, only one of the solenoids 54 is driven by a periodic power source, while the other solenoid, disposed at a 45° angle with respect to the center of the mirror 24 and the first solenoid, is driven by a slowly increasing voltage so that the mirror is progressively tilted in a direction that is perpendicular to the direction of oscillation.

Figure 8A:
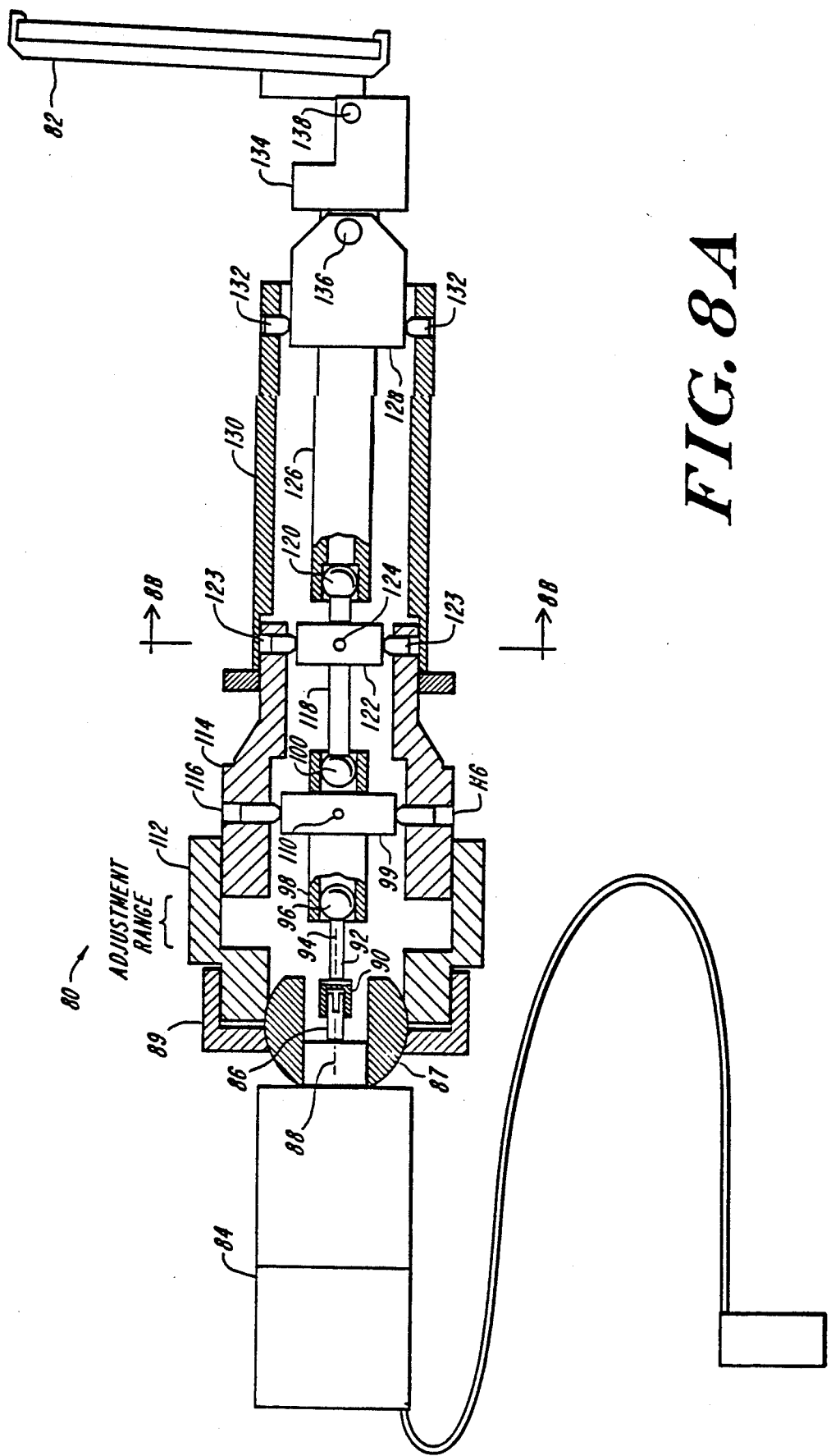
FIG. 8A is a cut-away side view of an embodiment for inclusion in a joy-stick controlled laser delivery system.

Referring to FIG. 8A, an alternate embodiment is shown that can be used as part of a joy-stick controlled laser system wherein a physician directs a surgical laser beam to a tissue site by means of a mirror controlled by the joy-stick assembly 80. In this embodiment, laser beam targeting is accomplished by manipulating the handle of the joy-stick which in this embodiment also serves as the motor 84, and cyclical scanning of the targeted laser beam is also performed by the assembly generally designated by reference numeral 80. The assembly 80 serves as the joy-stick assembly of a medical laser system such that movements of the motor 84 of the joy-stick assembly that would in the prior art typically result in orientation of a fixed mirror for directing a laser beam instead result in orientation of the cyclically scanned mirror 82. Furthermore, the assembly 80 such that its mirror assembly 82 is disposed in the path of the laser beam. Thus a scanned beam can be positioned by pivoting a the motor assembly 84 fixed to the ball 87 within the mounting collets 89 and 112.

Typically, the joystick assembly includes at least one gimbal assembly for orienting said orientable substrate with at least two degrees of freedom, this orientating being superimposed upon and occurring independently of the oscillating changes in mirror surface orientation produced by the assembly 80. The joystick assembly can be remotely actuated using solenoids that are driven to move the joystick with two degrees of freedom.

A motor assembly 84 is operative to rotate a shaft 86 about an axis 88. The shaft 86 is fixed to a coupler 90 which is mounted eccentrically such that a shaft 92 with a central axis 94 is effectively non-concentric with respect to the shaft 86. Thus, when the shaft 86 rotates, the shaft 92 and its axis 94 will describe a circular path centered on the axis 88. The shaft 94 terminates in a mounted ball 96. The ball 96 rides within a hollow sleeve 98 which receives a second mounted ball 100 at its opposing end. The sleeve 98 is mounted on a gimbal 99 that enables the sleeve to pivot with two degrees of freedom about a point 110. Rotation of the shaft 86 will result in a cyclical pivoting motion of the sleeve 98 through two degrees of freedom. Also, the sleeve 98 is mounted on the gimbal 99 such that more of its length extends from the gimbal 99 to the motor assembly 84 than extends from the gimbal away from the motor assembly 84. Consequently, the circular path of the ball 100 describes a path of smaller radius than the circular path described by the ball 96.

To adjust the amplitude of the cyclical pivoting motion of the sleeve 98, an outer sleeve 112 is operative to slidably receive an inner sleeve 114, and the sleeve 98 is operative to slidably receive the mounted ball 96. The gimbal 99 is mounted to the inner sleeve 114 by mean of conepoint setscrews 116. The sleeve 114 traverses an adjustment range with respect to sleeve 112, thereby enabling a user to adjust the size of a cyclical scanning pattern. For example, sliding the sleeve 114 into the sleeve 112 will decrease the distance of the ball 96 to the pivot point 110, thereby increasing the amplitude of the cyclical pivoting motion, and consequently increasing the size of the cyclical path described by the mounted ball 100, and ultimately increasing the size of a laser scan pattern at a targeted tissue site.

The second mounted ball 100 is fixed to a second shaft 118 that terminates in a third mounted ball 120. The shaft 118 is mounted on a gimbal 122 that enables the shaft 118 to pivot with two degrees of freedom about points 123 and 124. The gimbal 122 is mounted to the sleeve 114 by means of conepoint set screws 123. Also, the shaft 118 is mounted on the gimbal 122 such that more of its length extends from the gimbal 122 to the motor assembly 84 than extends from the gimbal away from the motor assembly 84. Consequently, the cyclical path of the ball 120 describes a path of smaller size than the path described by the ball 100. Furthermore, pivoting of the sleeve 98 results in a countercyclical pivoting motion of the shaft 118 through two degrees of freedom, such that the mounted balls 96 and 120 will oscillate in phase.

The ball 120 is disposed within a sleeve 126 that pivots with two degrees of freedom about points 132 and 136. A third gimbal 128 is fixed to the sleeve 130 via two gimbal mounts 132. The third gimbal 128 is adjustably connected to the mirror assembly 82 via an orientation adjuster 134. As with the gimbals 99 and 122, the gimbal 128 serves to further reduce the amplitude of the oscillation transmitted to the mirror assembly 82. The orientation of the mirror assembly 82 with respect to the gimbal 128 can be adjusted using a locking screw 138.

Figure 8B:
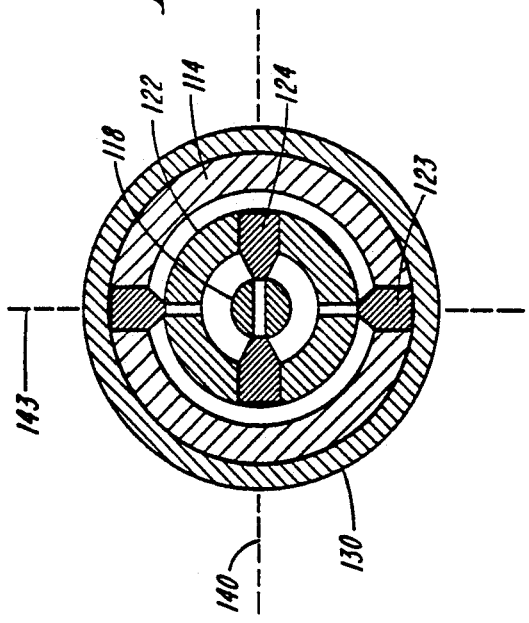
FIG. 8B is a detail of a gimbal included in the embodiment of FIG. 8A taken along the line 8B—8B.

Referring to FIG. 8B, a detailed view of the gimbal 122 along 8B—8B of FIG. 8A is provided. The shaft 118 can rotate about an axis 140 by means of inner pivot points 124. The pivots 124 are fixed to an inner ring 122. The inner ring 122 can rotate about an axis 143 by means of outer pivots 123. Pivots 123 are fixed to outer ring 114 that is fixed to an outer gimbal jacket 130. Since the pivots 123 and 124 operate independently, a rocking motion through two degrees of freedom is possible.

Figure 9:
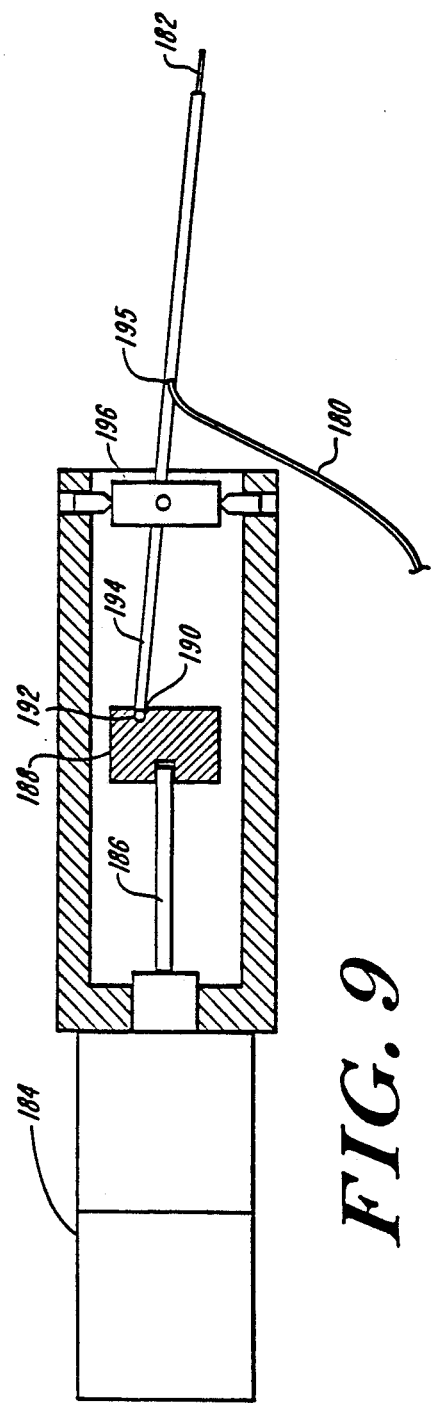
FIG. 9 is a cut-away side view of an embodiment for inclusion in a joy-stick controlled laser delivery system that employs an optical fiber for directing a laser beam.

With reference to FIG. 9, the medical laser system for scanning a beam of laser light can also include a beam-guiding optical fiber 180 with a transmissive tip 182, the fiber 180 being cooperative with means for cyclically oscillating the transmissive tip to cause a laser beam to be scanned in a cyclical or zig-zag pattern. The means for cyclically oscillating the tip 182 includes a motor 184 operative to rotate a shaft 186 that terminates in an eccentric collar 188. The collar 188 includes an off-axis cavity 190 that receives a terminating ball 192 such that the ball 192 can freely rotate within the cavity 190. The terminating ball 192 is fixed to an end of a shaft 194 that is mounted to a gimbal 196 that permits oscillatory motion of the shaft such as that described above for the embodiment of FIGS. 8A and 8B. The shaft 194 includes a hollow end with an insertion hole 195 that receives the optical fiber 180, allowing the transmissive tip 182 of the fiber 180 to emerge at the end of the shaft 194 opposite to the end with the terminating ball 192. Thus, operation of the motor 184 will cause the transmissive tip 182 to be scanned in a circular path, thereby scanning a laser beam transmitted by the tip 182 in a circular pattern upon a selected tissue site. A series of gimbals may also be included, as demonstrated in the embodiment of FIGS. 8A and 8B, to provide a reduced oscillation amplitude and concomitant reduced scan pattern radius. Also, this embodiment can be included in a joy-stick controlled laser delivery system.

Laser light of a wide variety of wavelengths can be employed, and for certain wavelengths, a dye or a chromophore can be applied to the tissue to enhance absorption of laser light, thereby enhancing its cutting action. Although a $CO_2$ laser has been used to describe the preferred embodiment, other type of lasers, including other infrared and visible lasers can also be used in conjunction with the invention. If a visible laser is employed instead of the $CO_2$ laser, it is not necessary to use a separate targeting beam such as the HeNe laser. Instead, the same visible laser beam can be used for both tissue removal and targeting. To accomplish this, the visible beam is attenuated so as not to induce tissue heating during a targeting phase.

Other modifications and implementations will occur to those skilled in the art without departing from the spirit and scope of the invention as claimed. Accordingly, the above description is not intended to limit the invention except as indicated in the following claims.

What is claimed is:

1. Apparatus for generating and directing a scanned beam of laser light comprising:
    a laser for providing a laser light beam;
    an orientable substrate including a surface adapted to substantially reflect said laser light beam, and positioned to receive said laser light beam, wherein said substrate is adapted to at least partially transmit visible light;
    oscillation means connected to said substrate for producing periodic changes in angular orientation of said substantially reflecting surface to cause scanning of said laser light beam in a cyclical pattern within a defined boundary; and
    directing means for directing said scanned beam of light onto a target.

2. The apparatus of claim 1 wherein said substantially reflecting surface is substantially planar.

3. Apparatus for generating and directing a scanned beam of laser light comprising:
    a laser for providing a laser light beam;
    an orientable substrate including a surface adapted to substantially reflect said laser light beam, and positioned to receive said laser light beam;
    oscillation means connected to said substrate for producing periodic changes in angular orientation of said substantially reflecting surface to cause scanning of said laser light beam in a cyclical pattern within a defined boundary, wherein said oscillation means comprises:
        a motor for inducing rotary motion of a shaft; and
        transmission means attached to said substrate and said shaft for causing a change in angular orientation of said substrate, wherein said transmission means comprises a mounting adapted to fix the reflecting surface of said substrate in non-perpendicular relationship with said shaft, wherein said mounting comprises a forked section including a plurality of off-axis members fixed to said substrate, disposed such that a central region in the vicinity of the substrate is substantially free of obstructions to the passage of laser light; and
    directing means for directing said scanned beam of light onto a target.

4. Apparatus for generating and directing a scanned beam of laser light comprising:
    a laser for providing a laser light beam;
    an orientable substrate including a surface adapted to substantially reflect said laser light beam, and positioned to receive said laser light beam;
    oscillation means connected to said substrate for producing periodic changes in angular orientation of said substantially reflecting surface to cause scanning of said laser light beam in a cyclical pattern within a defined boundary, wherein said oscillation means comprises:
        a motor for inducing rotary motion of a shaft; and
        transmission means attached to said substrate and said shaft for causing a change in angular orientation of said substrate, said transmission means comprising:
            moment means connected to said shaft and operative to dispose a first end of a projecting member, connected to said moment means, in an off-axis position relative to said shaft; and
            means for converting movements of a first amplitude of said moment means into smaller amplitude movements of said substrate.

5. Apparatus for generating and directing a scanned beam of laser light comprising:
    a laser for providing a laser light beam;
    an orientable substrate including a surface adapted to substantially reflect said laser light beam, and positioned to receive said laser light beam;

oscillation means connected to said substrate for producing periodic changes in angular orientation of said substantially reflecting surface to cause scanning of said laser light beam in a cyclical pattern within a defined boundary; and directing means for directing said scanned beam of light onto a target, wherein said directing means comprises at least one x-y positioning assembly for orienting said orientable substrate with at least two degrees of freedom, and independently of said oscillation means.

6. The apparatus of claim 5 wherein said directing means is a joystick assembly including one gimbal assembly that provides two degrees of freedom.

7. The apparatus of claim 5 wherein said directing means are remotely actuated using electromechanical means.

8. The apparatus of claim 7 wherein said electromechanical means are solenoids driven to move said x-y positioning assembly with two degrees of freedom.

* * * * *